US011167996B1

(12) United States Patent
Schmidt et al.

(10) Patent No.: US 11,167,996 B1
(45) Date of Patent: Nov. 9, 2021

(54) SYNTHESIS OF SZR FRAMEWORK TYPE MOLECULAR SIEVES

(71) Applicant: Chevron U.S.A. Inc., San Ramon, CA (US)

(72) Inventors: Joel Edward Schmidt, Oakland, CA (US); Cong-Yan Chen, Kensington, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 17/323,034

(22) Filed: May 18, 2021

Related U.S. Application Data

(60) Provisional application No. 63/033,943, filed on Jun. 3, 2020.

(51) Int. Cl.
| | | |
|---|---|---|
| *C01B 39/48* | (2006.01) | |
| *B01J 29/70* | (2006.01) | |
| *B01J 29/74* | (2006.01) | |
| *B01J 37/00* | (2006.01) | |
| *B01J 37/04* | (2006.01) | |
| *B01J 37/10* | (2006.01) | |
| *C07C 1/22* | (2006.01) | |
| *C07C 5/22* | (2006.01) | |
| *B01J 37/30* | (2006.01) | |

(52) U.S. Cl.
CPC .............. *C01B 39/48* (2013.01); *B01J 29/70* (2013.01); *B01J 29/74* (2013.01); *B01J 37/0018* (2013.01); *B01J 37/04* (2013.01); *B01J 37/10* (2013.01); *B01J 37/30* (2013.01); *C07C 1/22* (2013.01); *C07C 5/222* (2013.01); *B01J 2229/186* (2013.01); *B01J 2229/38* (2013.01); *C01P 2002/72* (2013.01); *C01P 2004/03* (2013.01)

(58) Field of Classification Search
CPC .. C01B 39/48; B01J 29/70; B01J 29/74; B01J 37/10; C01P 2002/72
See application file for complete search history.

(56) References Cited

U.S. PATENT DOCUMENTS

| | | |
|---|---|---|
| 5,118,483 A | 6/1992 | Barri |
| 10,399,066 B2 | 9/2019 | Chen et al. |

OTHER PUBLICATIONS

Zhou et al, "Synthesis of SUZ-4 zeolite by a dry gel conversion method", J. Porous Mater. (2013) 20:523-530 (Year: 2012).*
Paik et al, "Synthesis of zeolites P1 and SUZ-4 through a synergy of organic N,N,N,N ',N ',N '-hexaethylpentanediammonium and inorganic cations", Chem. Commun., 2000, 1609-1610 (Year: 2000).*
Zhang et al, "Organotemplate-free route for synthesizing SUZ-4 zeolite under static hydrothermal condition", Materials Research Bulletin 46 (2011) 1451-14541452 (Year: 2011).*
S.L. Lawton, J.M. Bennett, J.L Schlenker and M.K. Rubin "Synthesis and proposed framework topology of zeolite SUZ-4" J. Chem. Soc. Chem. Commun. 1993, 894-896.
D.B. Lukyanov, V.L. Zholobenko, J. Dwyer, S.A.I. Barri and W.J. Smith "On the Structural, Acidic and Catalytic Properties of Zeolite SUZ-4" J. Phys. Chem. B 1999, 103, 197-202.

(Continued)

*Primary Examiner* — David M Brunsman

(57) ABSTRACT

A method is provided for synthesizing molecular sieves of SZR framework type using 1,2,3-trimethylimidazolium cations as a structure directing agent and alumina-coated silica as a combined source of silicon and aluminum.

8 Claims, 8 Drawing Sheets

(56) References Cited

OTHER PUBLICATIONS

K.G. Strohmaier, M. Afeworki and D.L. Dorset "The crystal structures of polymorphic SUZ-4" Z. Krystallogr. 2006, 221, 689-698.
M. Dyballa, D.K. Pappas, E. Borfecchia, P. Beato, U. Olsbye, K.P. Lillerud, B. Arstad and S. Svelle "Tuning the material and catalytic properties of SUZ-4 zeolites for the conversion of methanol or methane" Micropor. Mesopor. Mater. 2018, 265, 112-122.

* cited by examiner

SYNTHESIS OF SZR FRAMEWORK TYPE MOLECULAR SIEVES

CROSS-REFERENCE TO RELATED APPLICATIONS

This application claims priority to and the benefit of U.S. Provisional Application Ser. No. 63/033,943, filed Jun. 3, 2020.

FIELD

This disclosure relates to methods for preparing SZR framework type molecular sieves.

BACKGROUND

Molecular sieves are a commercially important class of materials that have distinct crystal structures with defined pore structures that are shown by distinct X-ray diffraction (XRD) patterns and have specific chemical compositions. The crystal structure defines cavities and pores that are characteristic of the specific type of molecular sieve.

Crystalline microporous materials are classified by the Structure Commission of the International Zeolite Association according to the rules of the IUPAC Commission on Zeolite Nomenclature. According to this classification, framework type zeolites and other crystalline microporous crystalline materials, for which a structure has been established, are assigned a three-letter code and are described in the "*Atlas of Zeolite Framework Types*" (Sixth Revised Edition, Elsevier, 2007).

One known crystalline material for which a structure has been established is the material designated with the SZR framework type, most notably including SUZ-4. The three-dimensional pore system of SUZ-4 consists of a straight 10-membered ring (MR) pore and two intersecting 8-MR zigzag pores. Crystalline SUZ-4 and its conventional preparation using tetraethylammonium cations as a structure directing agent are taught by U.S. Pat. No. 5,118,483. Zeolite SUZ-4 has a needle-like morphology (see, e.g., S. L. Lawton et al., *J. Chem. Soc., Chem. Commun.* 1993, 894-896 and K. G. Strohmaier et al., Z *Krystallogr.* 2006, 221, 689-698). Zeolites having a needle-like morphology are undesirable due to their associated health concerns.

U.S. Pat. No. 10,399,066 discloses aluminosilicate SZR-framework type zeolites JMZ-5 and JMZ-6 having acicular and needle aggregate morphologies, respectively, and methods of their preparation.

According to the present disclosure, it has now been found that SZR framework type molecular sieves, particularly with improved morphology, can be prepared using 1,2,3-trimethylimidazolium cations as a structure directing agent and alumina-coated silica as a source of silicon and aluminum.

SUMMARY

In one aspect, there is provided a method of synthesizing a molecular sieve of SZR framework type, the method comprising: (1) preparing a reaction mixture comprising: (a) an alumina-coated silica; (b) a source of an alkali or alkaline earth metal (M); (c) a structure directing agent comprising 1,2,3-trimethylimidazolium cations (Q); (d) a source of hydroxide ions; and (e) water; and (2) subjecting the reaction mixture to crystallization conditions sufficient to form crystals of the molecular sieve.

In another aspect there is provided a molecular sieve of SZR framework type and, in its as-synthesized form, comprising 1,2,3-trimethylimidazolium cations in its pores.

DETAILED DESCRIPTION

Definitions

Figure 1:
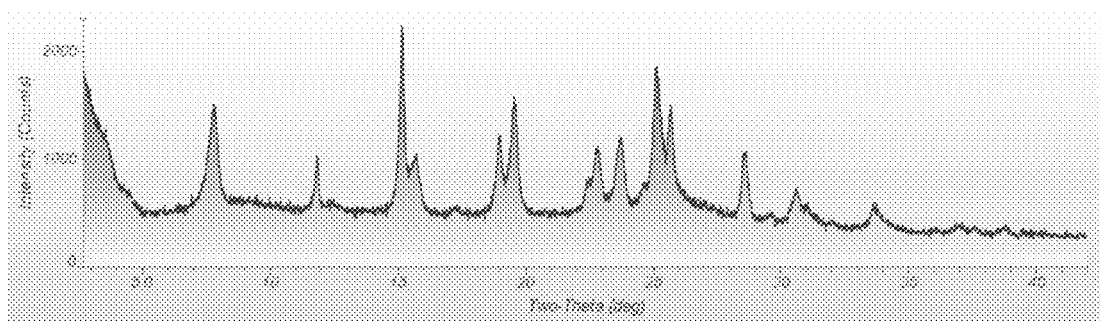
FIG. 1 shows a powder X-ray diffraction (XRD) pattern of the as-synthesized SZR framework type molecular sieve product of Example 1.

The term "molecular sieve" is used synonymously with the term "microporous crystalline material" or "zeolite".

The term "framework type" as used herein has the meaning described in the "*Atlas of Zeolite Framework Types*" by Ch. Baerlocher, L. B. McCusker and D. H. Olson (Elsevier, Sixth Revised Edition, 2007).

The term "as-synthesized" refers to a molecular sieve in its form after crystallization, prior to removal of the structure directing agent.

The term "anhydrous" refers to a molecular sieve substantially devoid of both physically adsorbed and chemically adsorbed water.

The term "$SiO_2/Al_2O_3$ molar ratio" may be abbreviated as "SAR".

Synthesis of the Molecular Sieve

A molecular sieve of SZR framework type can be synthesized by: (1) preparing a reaction mixture comprising: (a) an alumina-coated silica; (b) a source of an alkali or alkaline earth metal (M); (c) a structure directing agent comprising 1,2,3-trimethylimidazolium cations (Q); (d) a source of hydroxide ions; and (e) water; and (2) subjecting the reaction mixture to crystallization conditions sufficient to form crystals of the molecular sieve.

The reaction mixture can have a composition, in terms of molar ratios, within the ranges set forth in Table 1:

TABLE 1

| Reactants | Broadest | Secondary |
| --- | --- | --- |
| $SiO_2/Al_2O_3$ | 10 to 80 | 15 to 50 |
| $M/SiO_2$ | 0.05 to 0.50 | 0.10 to 0.35 |
| $Q/SiO_2$ | 0.01 to 0.05 | 0.02 to 0.05 |

TABLE 1-continued

| Reactants | Broadest | Secondary |
|---|---|---|
| OH/SiO$_2$ | 0.05 to 0.50 | 0.10 to 0.35 |
| H$_2$O/SiO$_2$ | 10 to 60 | 15 to 50 | wherein M is an alkali or alkaline earth metal and Q comprises 1,2,3-trimethylimidazolium cations.

The alumina-coated silica can be single type of alumina-coated silica or a mixture of two or more alumina-coated silica materials having different silica-to-alumina molar ratios. In some aspects, the colloidal aluminosilicate sol-gel is used as the sole or predominant source of silicon and aluminum. Alumina-coated silicas in a number of different SiO$_2$/Al$_2$O$_3$ molar ratios (e.g., 35, 80, 100, 127) are available from Nalco (Naperville, Ill.).

The alkali or alkaline earth metal (M) is typically introduced into the reaction mixture in conjunction with the source of hydroxide ions. Examples of such metals include sodium and/or potassium, and also lithium, rubidium, cesium, magnesium, and calcium. As used herein, the phrase "alkali or alkaline earth metal" does not mean the alkali metals and alkaline earth metals are used in the alternative, but instead that one or more alkali metals can be used alone or in combination with one or more alkaline earth metals and that one or more alkaline earth metals can be used alone or in combination with one or more alkali metals.

The structure directing agent comprises 1,2,3-trimethylimidazolium cations (Q), represented by the following structure (1):

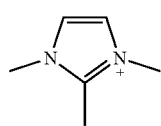

(1)

Suitable sources of Q the hydroxides, chlorides, bromides, and/or other salts of the quaternary ammonium compound.

The reaction mixture may comprise seeds of a crystalline material, such as an SZR framework type molecular sieve from a previous synthesis, desirably in an amount from 0.01 to 10000 wppm (e.g., 100 to 5000 wppm), based on the weight of the reaction mixture. Seeding can be advantageous to improve selectivity for SZR and/or to shorten the crystallization process.

It is noted that the reaction mixture components can be supplied by more than one source. Also, two or more reaction components can be provided by one source. The reaction mixture can be prepared either batchwise or continuously.

Crystallization of the desired molecular sieve from the above reaction mixture can be carried out under either static, tumbled or stirred conditions in a suitable reactor vessel, such as for example polypropylene jars or Teflon-lined or stainless-steel autoclaves, at a temperature of from 100° C. to 200° C. (e.g., 150° C. to 180° C.) for a time sufficient for crystallization to occur at the temperature used, e.g., from about 1 day to 14 days. Crystallization is usually conducted under pressure in an autoclave so that the reaction mixture is subject to autogenous pressure.

Once the desired molecular sieve crystals have formed, the solid product can be separated from the reaction mixture by standard mechanical separation techniques such as centrifugation or filtration. The crystals can be water-washed and then dried to obtain the as-synthesized molecular sieve crystals. The drying step can be performed at an elevated temperature (e.g., 75° C. to 150° C.) for several hours (e.g., 4 to 24 hours). The drying step can be performed under vacuum or at atmospheric pressure.

As a result of the crystallization process, the recovered crystalline molecular sieve product contains within its pores at least a portion of the structure directing agent used in the synthesis.

The as-synthesized molecular sieve may be subjected to thermal treatment, ozone treatment, or other treatment to remove part or all of the structure directing agent used in its synthesis. Removal of the structure directing agent may be carried out by thermal treatment (i.e., calcination) in which the as-synthesized molecular sieve is heated in air or inert gas at a temperature sufficient to remove part or all of the structure directing agent. While sub-atmospheric pressure may be used for the thermal treatment, atmospheric pressure is desired for reasons of convenience. The thermal treatment may be performed at a temperature at least 370° C. for at least a minute and generally not longer than 20 hours (e.g., from 1 to 12 hours). The thermal treatment can be performed at a temperature of up to 925° C. For example, the thermal treatment may be conducted at a temperature of 400° C. to 600° C. in air for approximately 1 to 8 hours.

Any extra-framework metal cations in the molecular sieve may be replaced in accordance with techniques well known in the art (e.g., by ion exchange) with other cations. Replacing cations can include metal ions, hydrogen ions, hydrogen precursor ions (e.g., ammonium ions), and combinations thereof.

The present SZR framework type molecular sieve can be formulated into a catalyst composition by combination with other materials, such as binders and/or matrix materials, which provide additional hardness or catalytic activity to the finished catalyst. When blended with such components, the relative proportions of the SZR framework type molecular sieve and matrix may vary widely with the content of the SZR framework type molecular sieve ranging from 1 to 90 wt. % (e.g., from 2 to 80 wt. %) of the total composite.

Characterization of the Molecular Sieve

In its as-synthesized and anhydrous form, the SZR framework type molecular sieve prepared as described herein can have a chemical composition, in terms of molar ratios, within the ranges set forth in Table 2:

TABLE 2

| | Broadest | Secondary |
|---|---|---|
| SiO$_2$/Al$_2$O$_3$ | 10 to 80 | 15 to 50 |
| Q/SiO$_2$ | >0 to 0.1 | >0 to 0.1 |
| M/SiO$_2$ | >0 to 0.1 | >0 to 0.1 | wherein Q comprises 1,2,3-trimethylimidazolium cations and M is an alkali or alkaline earth metal.

EXAMPLES

The following illustrative examples are intended to be non-limiting.

Example 1

Synthesis of SZR-Type Zeolite 3.8 g of 1 N KOH was combined with 0.29 g of 1,2,3-trimethylimidazolium hydroxide (2.16 mmol OH/g), 2.86 g of deionized water and finally 4.00 g of Nalco alumina-coated silica DVSZN007 (SAR=35; 24.5% solids). The final reaction mixture had a composition, in terms of molar ratios, as follows:

1 $SiO_2$:0.0286 $Al_2O_3$:0.24 KOH:0.04 Q-OH:34 $H_2O$.

The mixture was well mixed, sealed in an autoclave, and heated at 170° C. for 6 days with rotation at 43 rpm. The material was recovered by filtration and washed with copious amounts of water and finally dried in air at 85° C.

Figure 2A:
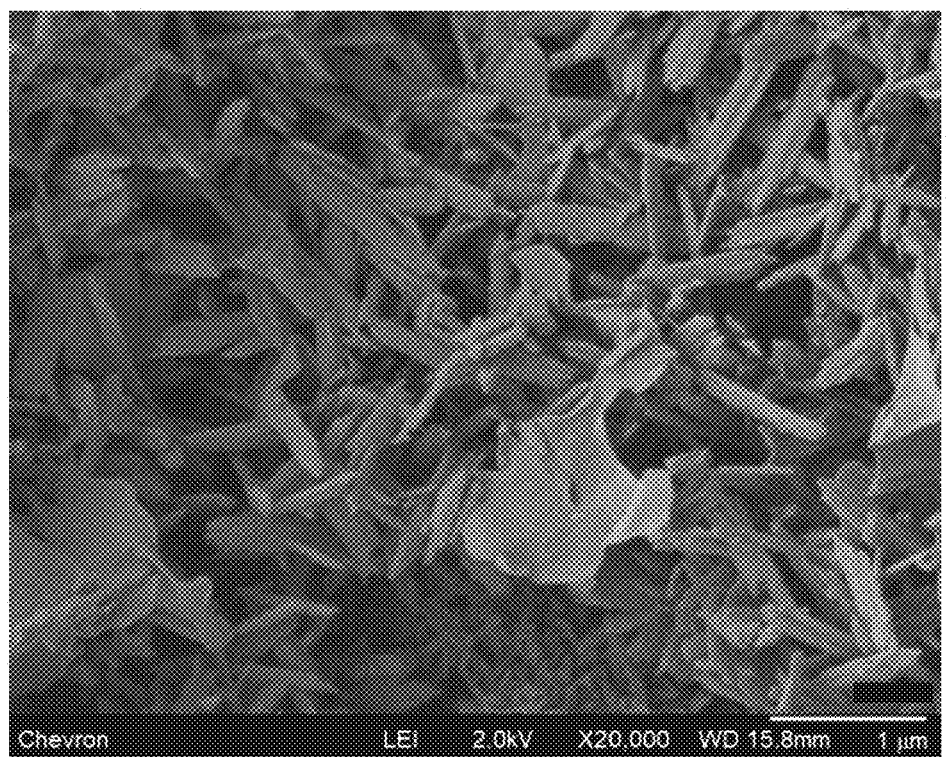
FIGS. 2(A) and 2(B) show Scanning Electron Micrograph (SEM) images of the as-synthesized SZR framework type molecular sieve product of Example 1 at various magnifications.
Figure 2B:
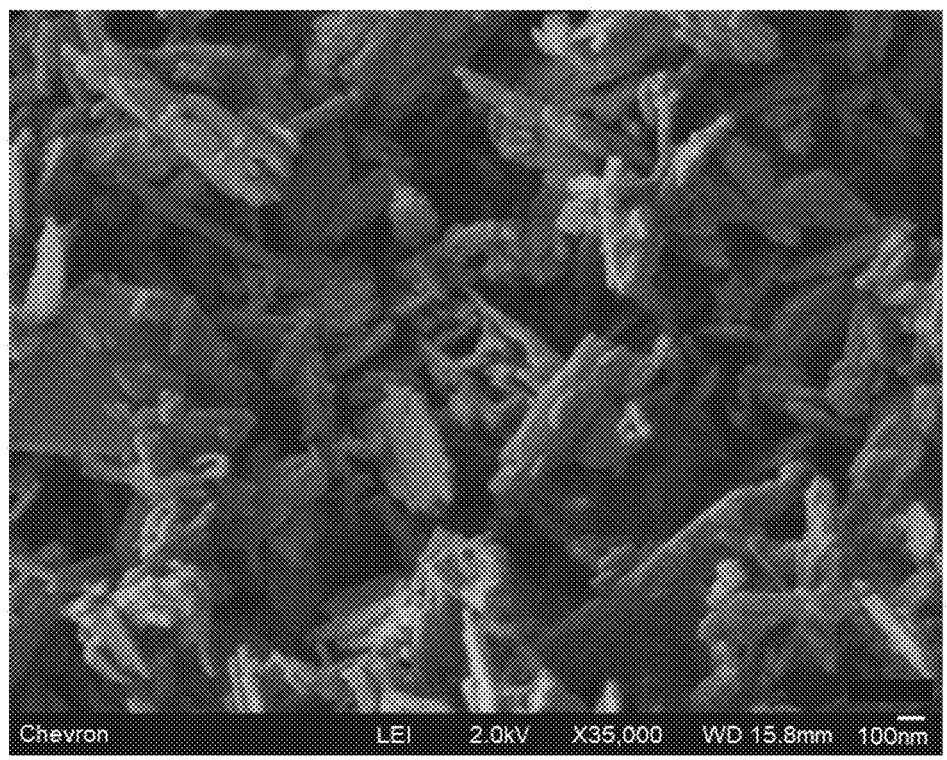

The resulting product was analyzed by powder XRD and SEM. The powder XRD pattern is shown in FIG. 1 and indicates that the material is a pure SZR zeolite. SEM images of the product at various magnifications are shown in FIGS. 2(A) and 2(B). FIGS. 2(A) and 2(B) show a material that does not have a high aspect ratio needle morphology.

Example 2 (Comparative)

Synthesis of Zeolite SUZ-4

As a comparative example, zeolite SUZ-4 was synthesized following Example 1 of U.S. Pat. No. 10,399,066 by combining 5.8 g of deionized water with 1.15 g of 45 wt. % KOH and then dissolving 0.06 g of aluminum foil. After dissolution, 0.93 g of 35 wt. % tetraethylammonium hydroxide was added followed by 4.88 g of LUDOX® AS-30 colloidal silica. The mixture was well homogenized, sealed in an autoclave and heated for 4 days at 150° C. with rotation at 43 rpm. The material was recovered by filtration and washed with copious amounts of water and finally dried in air at 85° C.

Figure 3:
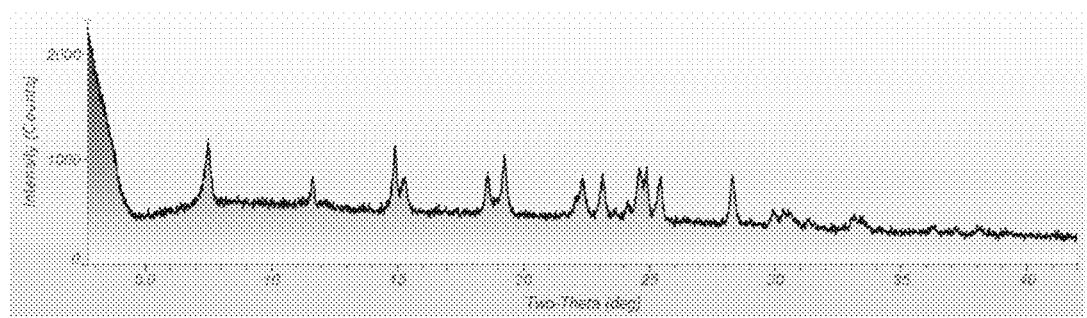
FIG. 3 shows a powder XRD pattern of zeolite SUZ-4 prepared according to U.S. Pat. No. 10,399,066.
Figure 4A:
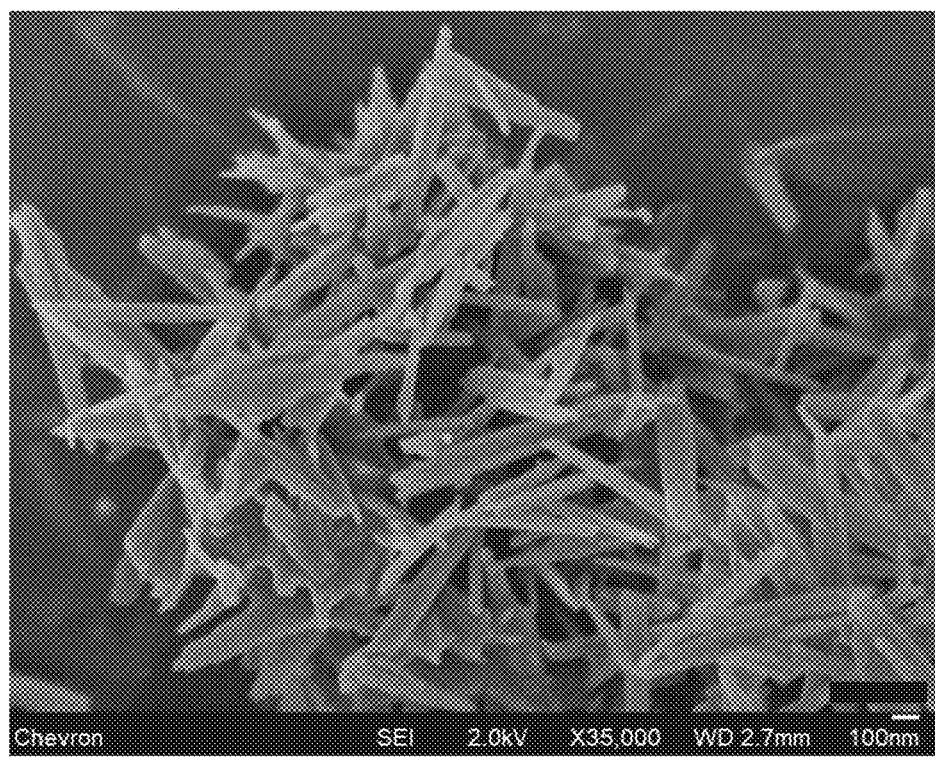
FIGS. 4(A) and 4(B) show SEM images of zeolite SUZ-4 prepared according to U.S. Pat. No. 10,399,066 at various magnifications.
Figure 4B:
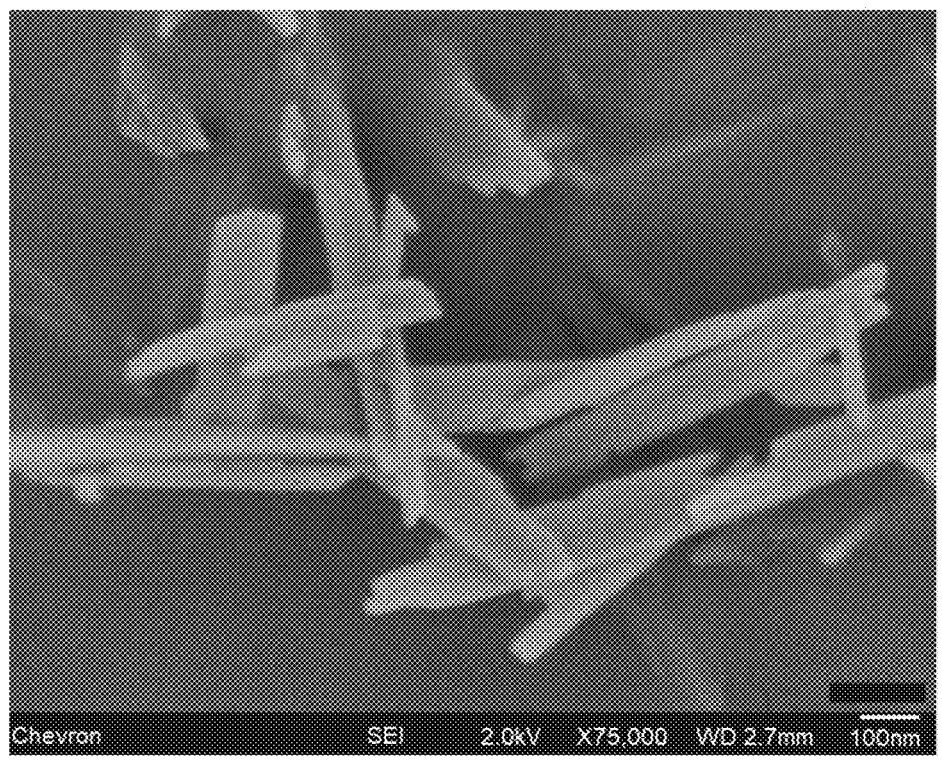

The resulting product was analyzed by powder XRD and SEM. The powder XRD pattern is shown in FIG. 3 and indicates that the material is a pure SUZ-4 zeolite. SEM images of the product at various magnifications are shown in FIGS. 4(A) and 4(B). FIGS. 4(A) and 4(B) show a material having a high aspect ratio needle morphology.

Example 3

Calcination of SZR-Type Zeolite

The as-synthesized material from Example 1 was calcined in air by placing a thin bed in a calcination dish and heating in a muffle furnace from room temperature to 120° C. at a rate of 1° C./minute and held at 120° C. for 2 hours. Then, the temperature was ramped up to 540° C. at a rate of 1° C./minute and held at 540° C. for 5 hours. The temperature was ramped up again at 1° C./minute to 595° C. and held at 595° C. for 5 hours. The material was then allowed to cool to room temperature.

Example 4

Ammonium-Ion Exchange of SZR-Type Zeolite

Figure 5:
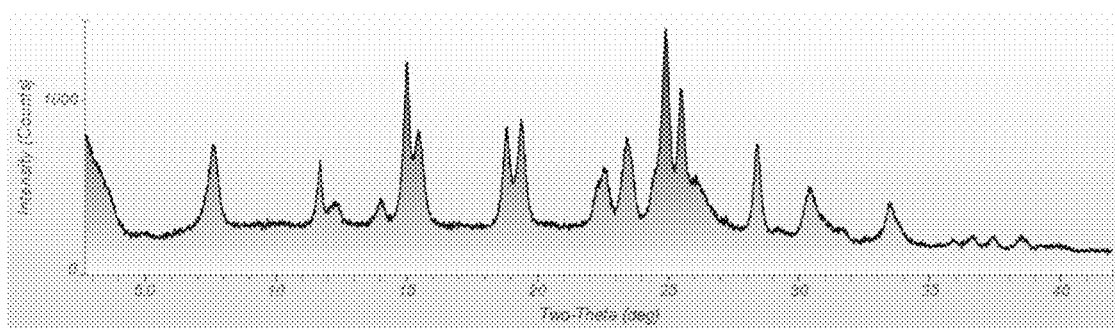
FIG. 5 shows a powder XRD pattern of the ammonium-form SZR framework type molecular sieve of Example 4.

The potassium form of the as-synthesized material from Example 3 was converted to the ammonium form by heating in a solution of ammonium nitrate (typically 1 g $NH_4NO_3$/1 g zeolite in 10 mL of $H_2O$ at 85° C. for at least 3 hours). The material was then filtered. This was repeated twice for a total of 3 exchanges. At the end, the material was washed with deionized water until the water conductivity of less than 10 ρS/cm. A powder XRD pattern of the ammonium exchanged product is shown in FIG. 5.

The product after drying was subjected to micropore volume analysis using N2 as the adsorbate and via the BET method. The zeolite had a micropore volume of 0.13 $cm^3$/g.

The acid site density was characterized using n-propylamine temperature programmed desorption (TPD) and found to be 525 μmol $H^+$/g.

As determined by Inductively Coupled Plasma-Atomic Emission Spectroscopy (ICP-AES) elemental analysis, the product had a $SiO_2/Al_2O_3$ molar ratio of 33.6 and a K/Al molar ratio of 0.23, indicating that not all potassium could be removed by ammonium exchange. This amount of non-exchangeable sites is consistent with previous findings. See, for example, D. B. Lukyanov et al. (*J. Phys. Chemistry B* 1999, 103, 197-202).

Example 5 (Comparative)

Calcination of Zeolite SUZ-4

The as-synthesized material from Example 2 was calcined in the same manner as described in Example 3.

Example 6 (Comparative)

Ammonium-Ion Exchange of Zeolite SUZ-4

Figure 6:
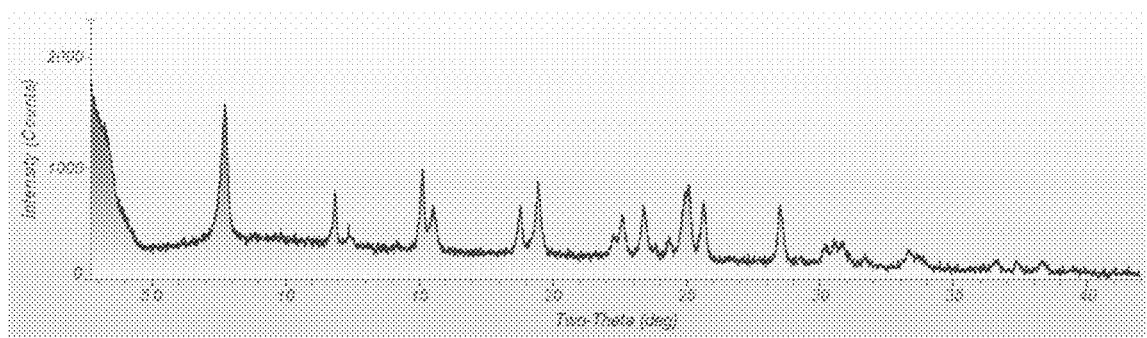
FIG. 6 shows a powder XRD pattern of the ammonium-form SUZ-4 zeolite of Example 5.

The potassium form of the as-synthesized SUZ-4 material from Example 5 was converted to the ammonium form using the method described in Example 4. FIG. 6 shows a powder XRD pattern of the ammonium-ion exchanged material.

Example 7

Palladium Exchange

For the palladium exchange to 0.5 wt. % Pd, 0.8 g of ammonium form material prepared in Example 4 was combined with 7.44 g of deionized water and 3.48 g of 0.156 N $NH_4OH$ solution followed by 0.80 g of palladium solution that was prepared by combining 0.36 g of tetraamminepalladium(II) nitrate in 21 g of deionized water and 3 g of 0.148 N $NH_4OH$ solution. The pH was then checked and, if necessary, adjusted to 10 by adding concentrated ammonium hydroxide dropwise until a pH of 10 was reached. After standing at room temperature for 3 days, the pH was checked again and if necessary readjusted to 10 and allowed to sit for 1 more day. The material was recovered by filtration, washed with deionized water, and dried in air overnight at 85° C. The Pd form material was calcined in dry air by heating at 1° C./minute ramp to 120° C. and holding at 120° C. or 180 minutes, and then heating at 1° C./minute ramp to 482° C. and holding 482° C. for 180 minutes. Finally, the material was pelletized at 5 kpsi, crushed and sieved to 20-40 mesh.

Example 8

Methanol-to-Hydrocarbons Conversion of SZR-Type Zeolite

For the methanol to hydrocarbons catalytic testing, the ammonium form of the material from Example 4 was pelletized at 5 kpsi, crushed and sieved to 20-40 mesh. 0.20 g of the dehydrated catalyst as determined by thermogravimetric analysis (TGA) at 600° C. (diluted 4:1 v/v with alundum) was centered in a down-flow stainless steel tube reactor in a split tube furnace. The catalytic reaction was carried out at atmospheric pressure. The catalyst was preheated in-situ under flowing nitrogen at 400° C. A feed of pure methanol was introduced into the reactor at a rate of 0.324 mL/h for 1.3 h$^{-1}$ WHSV in a 30 mL/minute flow of nitrogen as carrier gas. Reaction products from the product flow coming from the reactor outlet were injected automatically into an on-line Agilent gas chromatograph with a flame ionization detector and analyzed in-situ. The results are set forth in Table 3.

TABLE 3

| Methanol-to Hydrocarbons Conversion Catalytic Data | | | | | | | | |
|---|---|---|---|---|---|---|---|---|
| Time on Stream [h] | 0.5 | 0.9 | 1.2 | 1.6 | 1.9 | 2.3 | 2.6 | 3.0 |
| Conversion [%] | 81 | 80 | 80 | 80 | 80 | 80 | 80 | 80 |
| Yield [wt. %] | | | | | | | | |
| Dimethyl ether | 59 | 74 | 76 | 77 | 77 | 78 | 78 | 78 |
| C1-C3 Paraffins | 9.22 | 3.04 | 1.96 | 1.54 | 1.32 | 1.17 | 1.09 | 1.03 |
| Ethylene | 5.77 | 1.54 | 0.96 | 0.77 | 0.65 | 0.58 | 0.53 | 0.50 |
| Propylene | 2.7 | 0.6 | 0.3 | 0.3 | 0.2 | 0.2 | 0.2 | 0.1 |
| Butanes and Butenes | 1.13 | 0.22 | 0.14 | 0.14 | 0.12 | 0.07 | 0.06 | 0.08 |

Example 9

Constraint Index Determination of SZR Framework Type Zeolite

The ammonium form of the SZR framework type molecular sieve of Example 4 was pelletized at 4-5 kpsi and crushed and meshed to 20-40. Then, 0.47 g of the dehydrated catalyst as determined by TGA at 600° C. was packed into a ½ inch stainless steel tube with alundum on both sides of the molecular sieve bed. A Lindburg furnace was used to heat the reactor tube. Helium was introduced into the reactor tube at 10 mL/minute and at atmospheric pressure. The reactor was heated to about 371° C. and a 50/50 (w/w) feed of n-hexane and 3-methylpentane was introduced into the reactor at a rate of 8 µL/minute with a helium carrier gas of 10 mL/minute. Feed delivery was made via an ISCO pump. Direct sampling into a gas chromatograph (GC) began after 15 minutes of feed introduction.

The Constraint Index value calculated from the GC data using methods known in the art and was found to be between 2.87 and 3.39 for times on stream from 15 to 225 minutes (conversion less than 30%), which is characteristic for 10-membered ring molecular sieves.

Example 10 (Comparative)

Constraint Index Determination of SUZ-4 Zeolite

The Constraint Index value (excluding 2-methylpentane) of the SUZ-4 zeolite of Example 6 was measured in the same manner as described in Example 9 and was found to be between 1.72 and 2.65 for times on stream from 15 to 225 minutes (conversion less than 30%), which is characteristic for 10-membered ring molecular sieves.

Example 11

Hydroconversion of n-Decane

Figure 7:
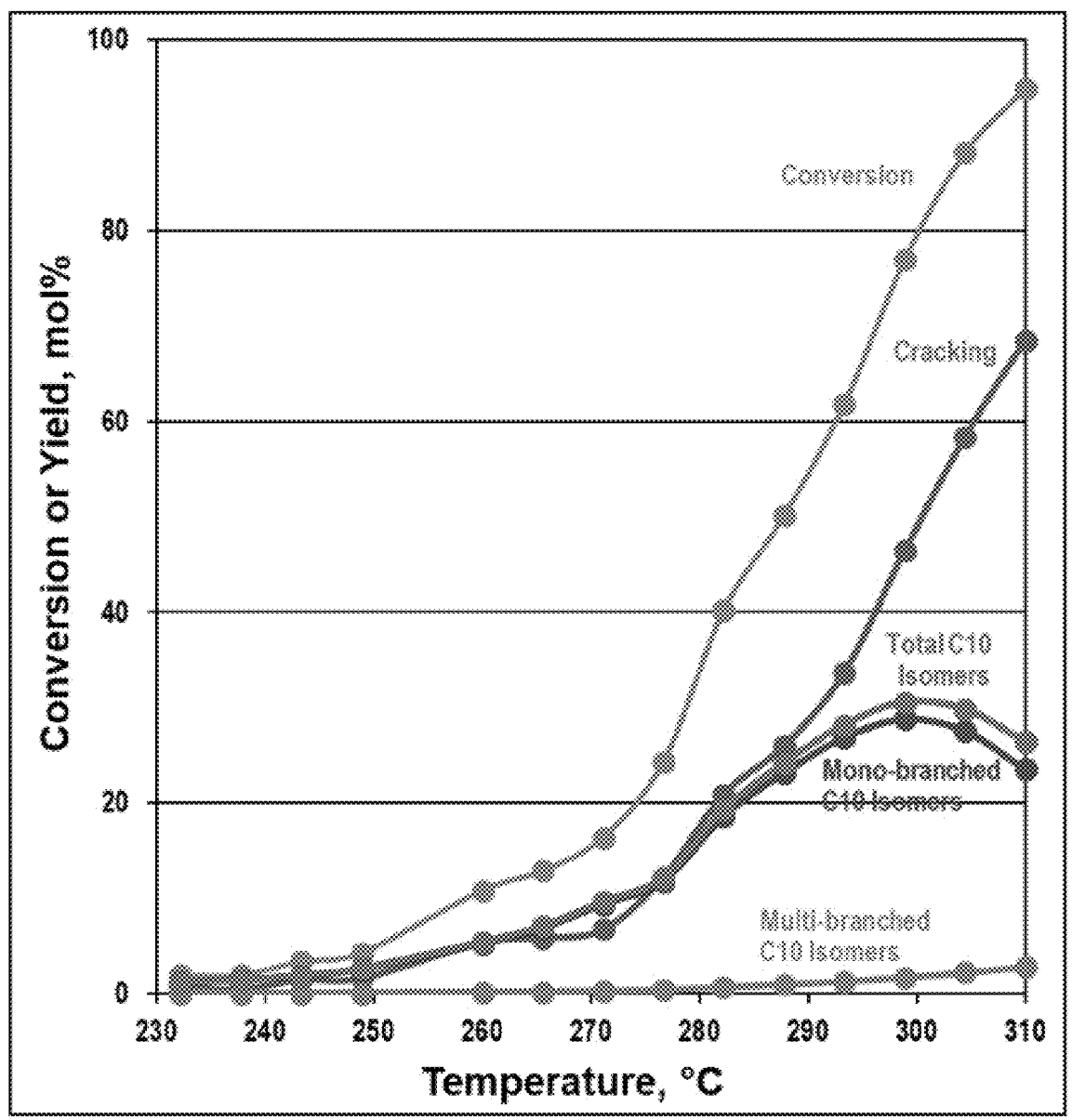
FIG. 7 is a graph illustrating the relationship between conversion or yield and temperature for hydroconversion of n-decane with a Pd/SZR catalyst.
Figure 8:
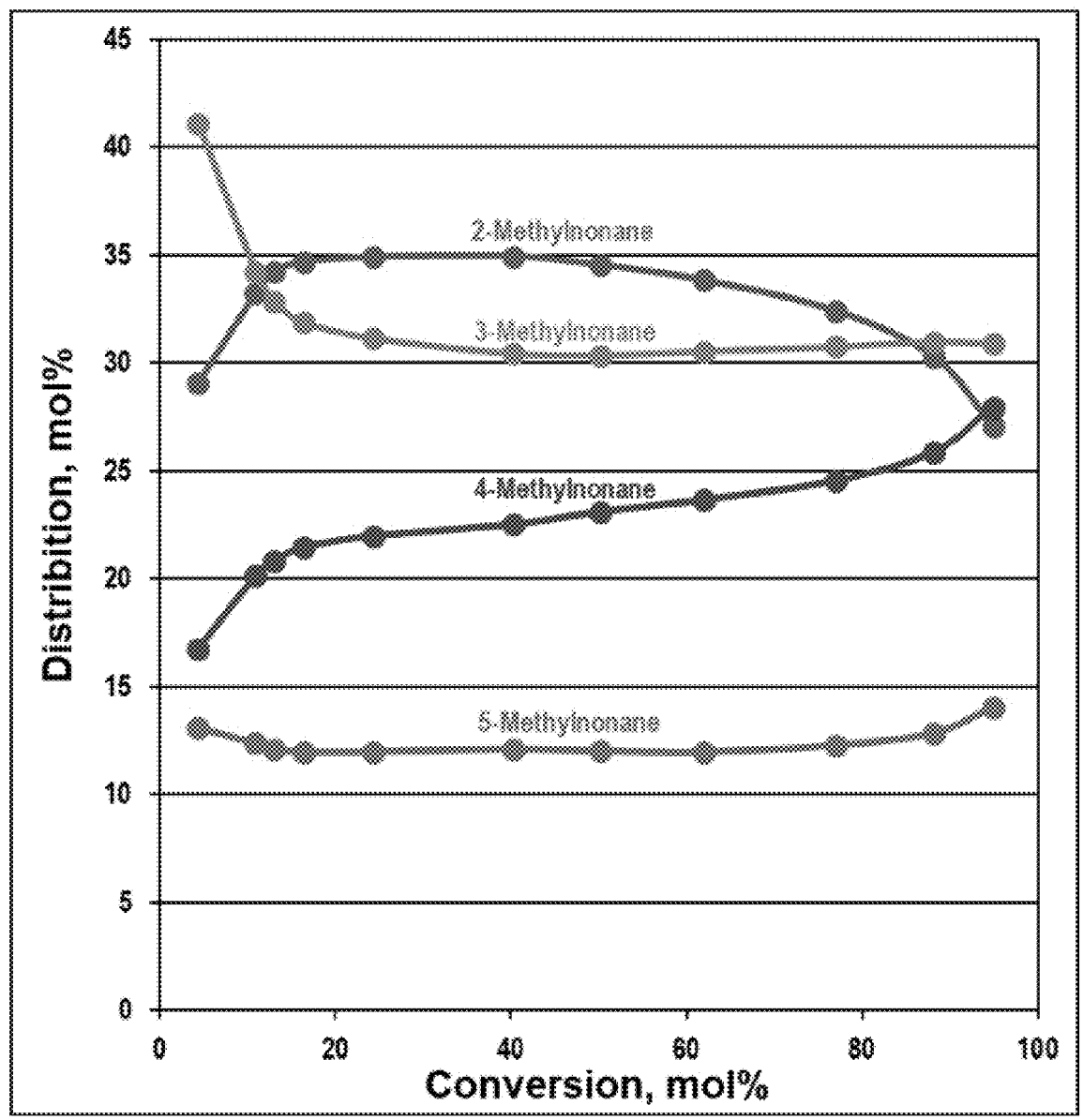
FIG. 8 is a graph illustrating the relationship between distribution of C10 mono-branched isomer products and conversion for hydroconversion of n-decane with a Pd/SZR catalyst.

For catalytic testing, 0.5 g of the Pd/SZR catalyst (weight of the dehydrated sample as determined by TGA at 600° C.) from Example 7 was loaded in the center of a 23 inch-long× ¼ inch outside diameter stainless steel reactor tube with alundum loaded upstream of the catalyst for preheating the feed (a total pressure of 1200 psig; a down-flow hydrogen rate of 12.5 mL/minute, when measured at 1 atmosphere pressure and 25° C.; and a down-flow liquid feed rate of 1 mL/hour). The catalyst was first reduced in flowing hydrogen at 315° C. for 1 hour. The reaction was carried out from 230° C. to 310° C. Products were analyzed by on-line capillary GC approximately once every 60 minutes. Raw data from the GC was collected by an automated data collection/processing system and hydrocarbon conversions were calculated from the raw data. Conversion is defined as the amount n-decane reacted in mol % to produce other products (including iso-C10). The yield of iso-C10 is expressed as mole percent of products other than n-decane. The yield of cracking products (smaller than C10) is expressed as mole percent of n-decane converted to cracking products. The results are shown in FIG. 7 and FIG. 8.

The invention claimed is:

1. A method of synthesizing a molecular sieve of SZR framework type, the method comprising:
   (1) preparing a reaction mixture comprising:
      (a) an alumina-coated silica;
      (b) a source of an alkali or alkaline earth metal (M);
      (c) a structure directing agent comprising 1,2,3-trimethylimidazolium cations (Q);
      (d) a source of hydroxide ions;
      (e) water; and
   (2) subjecting the reaction mixture to crystallization conditions sufficient to form crystals of the molecular sieve.

2. The method of claim 1, wherein the reaction mixture has a composition, in terms of molar ratios, as follows:

| | |
|---|---|
| $SiO_2/Al_2O_3$ | 10 to 80 |
| $M/SiO_2$ | 0.05 to 0.50 |
| $Q/SiO_2$ | 0.01 to 0.05 |
| $OH/SiO_2$ | 0.05 to 0.50 |
| $H_2O/SiO_2$ | 10 to 60. |

3. The method of claim 1, wherein the reaction mixture has a composition, in terms of molar ratios, as follows:

| | |
|---|---|
| $SiO_2/Al_2O_3$ | 15 to 50 |
| $M/SiO_2$ | 0.10 to 0.35 |
| $Q/SiO_2$ | 0.02 to 0.05 |
| $OH/SiO_2$ | 0.10 to 0.35 |
| $H_2O/SiO_2$ | 15 to 50. |

4. The method of claim 1, wherein the alkali or alkaline earth metal (M) comprises potassium.

5. The method of claim 1, wherein the crystallization conditions include a temperature of from 100° C. to 200° C. and a time of from 1 day to 14 days.

6. A molecular sieve of SZR framework type, and, in its as-synthesized form, comprising 1,2,3-trimethylimidazolium cations in its pores.

7. The molecular sieve of claim 6, having a molar ratio of $SiO_2/Al_2O_3$ in a range of from 10 to 80.

8. The molecular sieve of claim 6, having a molar ratio of $SiO_2/Al_2O_3$ in a range of from 15 to 50.

\* \* \* \* \*